United States Patent [19]

Pompei

[11] Patent Number: 5,081,359
[45] Date of Patent: Jan. 14, 1992

[54] DIFFERENTIAL THERMAL SENSOR

[75] Inventor: Francesco Pompei, Boston, Mass.

[73] Assignee: Exergen Corporation, Newton, Mass.

[21] Appl. No.: 527,175

[22] Filed: May 23, 1990

[51] Int. Cl.[5] .................................................. G01J 5/26
[52] U.S. Cl. ................................ 250/349; 250/338.1; 374/121
[58] Field of Search ................ 250/340, 338.1, 342, 250/349; 374/124, 126, 121, 112

[56] References Cited

U.S. PATENT DOCUMENTS

| | | | |
|---|---|---|---|
| 2,392,873 | 1/1946 | Zahl | 250/1 |
| 3,023,398 | 2/1962 | Ziegert | 340/51 |
| 4,030,362 | 6/1977 | Dimeff | 73/355 |
| 4,082,898 | 7/1977 | Janssen | 136/224 |
| 4,121,459 | 10/1978 | MaCall et al. | 73/340 |
| 4,345,840 | 8/1982 | Goetz et al. | 356/407 |
| 4,350,166 | 9/1982 | Mobarry | 128/664 |
| 4,746,224 | 5/1988 | Mizuno et al. | 374/124 |
| 4,831,258 | 5/1989 | Paulk et al. | 374/121 |
| 4,849,885 | 7/1989 | Stillwagon et al. | 128/736 |
| 4,895,164 | 1/1990 | Wood | 128/736 |

OTHER PUBLICATIONS

Amperes/Phillips Flyer on Low Profile IR Sensors.
Amperex Electronic Corporation Technical Publication No. 147, pp. 1-5, Feb. 1985.
Exergen Corporation Electronic Schematic of Sensor Circuit Jul. 9, 1986.
Exergen Corporation Electronics Schematic by M. B., Oct. 1, 1986.

*Primary Examiner*—Janice A. Howell
*Assistant Examiner*—Richard Hanig
*Attorney, Agent, or Firm*—Hamilton, Brook, Smith & Reynolds

[57] ABSTRACT

A differential temperature sensor uses two different thermopiles each encased in its own can. The thermopiles are given a position and spatial orientation to best suit the measuring task. A connector of low thermal impedance thermally connects the cold junctions of the two thermopiles. The connector is adjusted, angled or pivoted to allow the proper relative orientation of the thermopiles. The thermopiles are placed close to the detected areas to keep the thermopile cold junctions and a detected reference area close in temperature. An automatic assembly process uses the present invention in conjunction with a photoelectric switch which confirms the presence of the subject being measured. An improved chiropractic measuring device also uses the differential sensor to accurately sense nerve damage near the spine.

56 Claims, 6 Drawing Sheets

DIFFERENTIAL THERMAL SENSOR

BACKGROUND OF THE INVENTION

The ability of radiation detectors to operate as thermal detectors has allowed them to be used as non-contact alternatives to many conventional temperature sensors. For example, infrared sensing devices are being used in industrial applications to detect temperature differences between neighboring target locations. Such applications might include measuring heat gain or loss from machinery, plumbing or electrical lines. Typically, radiation sensors respond to changes in thermal radiation in the order of less than 1/10 second. This speed allows the sensors to operate in a quickly changing detection environment, further increasing their desirability.

One particular application of radiation detector use is in the quality control environment. The sensors can be used to detect a dynamic pattern of temperatures or temperature changes as found on assembly line and conveyor belt processes. A detector suitable for such a process is described in U.S. Pat. No. 4,831,258 to Paulk et al., and assigned to the assignee of the present invention. This detector is shown in FIG. 1 being used in conjunction with the quality control testing of a hot adhesive application process. A hot adhesive dispenser 12 applies adhesive 16 onto a substrate 9, such as a portion of a box top or other packaging piece. A dual element sensor 10 is mounted beside and downstream of the dispenser 12 and houses thermopiles 74 and 76.

The thermopiles 74. 76 of the sensor 10 are packaged together in a common can 77 with their cold junctions held at a common temperature. Through a lens 82 and aperture 79 in one end of sensor 10, thermopile 74 detects the thermal radiation of the dispensed adhesive target and thermopile 76 detects the thermal radiation of the adjacent reference portion 18 of the substrate 9 which does not have adhesive applied to it. With the two thermopiles coupled electrically in series, the dual element sensor 10 produces a signal of the thermal difference between the detected adhesive and substrate reference area 18. This signal is transmitted to remote display meter 22 by line 24. Meter 22 provides an LED bar graph display 26 of the sensed thermal difference and provides 2 sets of 3 LED displays 29 on opposite adjacent sides of the bar graph display 26. Hence, an indication of sensed heat flux can be seen by the user from three different sides of display meter 22.

SUMMARY OF THE INVENTION

The dual sensor detector of FIG. 1 is applicable to a number of different industrial applications, but is limited by the relative arrangement of the thermopiles 74, 76 in the common can. The common can guarantees a common cold junction temperature but makes it impossible to adjust the relative positioning of the thermopiles 74, 76. A focusing system is necessary to adapt the system to targets which are of different temperature and thus necessarily spaced apart. The system is additionally limited in that it is not adaptable to targets which face significantly different directions. The size of the thermopiles, the distance of the thermopiles from each other and from the targets, and the focusing power of the lens are interdependent with the location of the targets relative to one another and the size of the targets. There is little geometric flexibility.

In the present invention, a radiation detector has a first thermopile in a first can. The first thermopile senses thermal radiation from a target area and generates a signal indicative of the target area radiation. The detector also has a second thermopile in a second can. The second thermopile senses thermal radiation from a reference area and generates a signal indicative of the reference area radiation. The cold junction of the first thermopile and the cold junction of the second thermopile are thermally connected by a connector of low thermal impedance. Both thermopile cans and the connector are in a thermally isolated housing. An output signal is developed by the radiation detector using the signal generated by the first thermopile and the signal generated by the second thermopile. The output signal is indicative of thermal difference between the target area and the reference area.

The thermal connector between the cold junctions has a low thermal impedance which is three orders of magnitude less than (about $10^{-3}$ times) the thermal impedance through the housing between the cold junctions of the thermopiles and the ambient atmosphere. The connector within the insulated housing allows great displacement of the targets without the need for a lens. Without the lens, the thermopiles can be placed proximate to the area being sensed and therefore have a cold junction temperature close to the temperature of the reference target for improved sensitivity. In preferred embodiments, the connector is adjustable in length or pivotable to allow the proper orientation of the thermopiles. The developed output signal is displayed on a visual display such as an LED display. If desired, an alarm may be provided which is triggered when the output signal exceeds a predetermined limit.

DETAILED DESCRIPTION OF THE PREFERRED EMBODIMENTS

Figure 1:
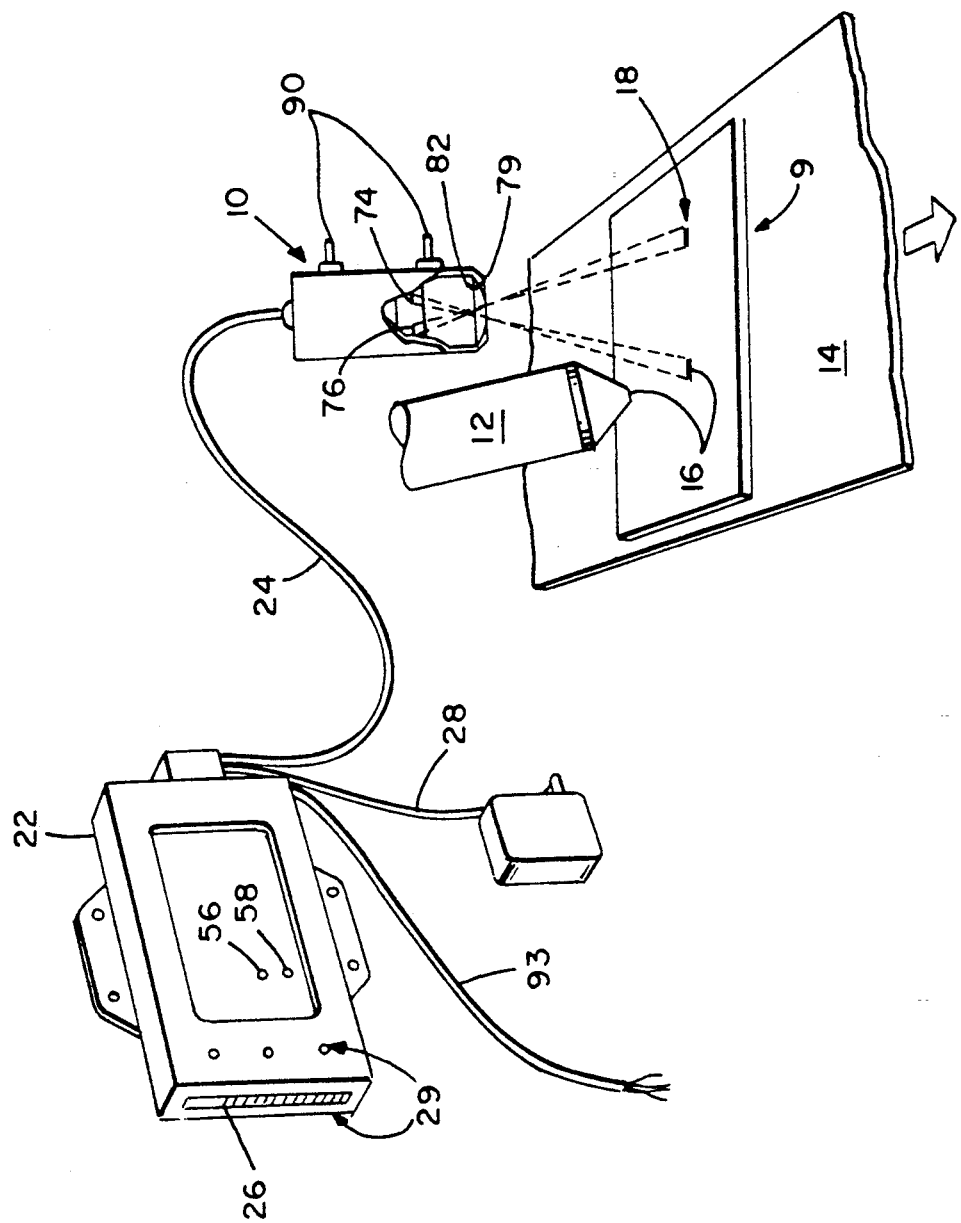
FIG. 1 is a perspective view of a prior art dual sensor radiation detector.
Figure 2:
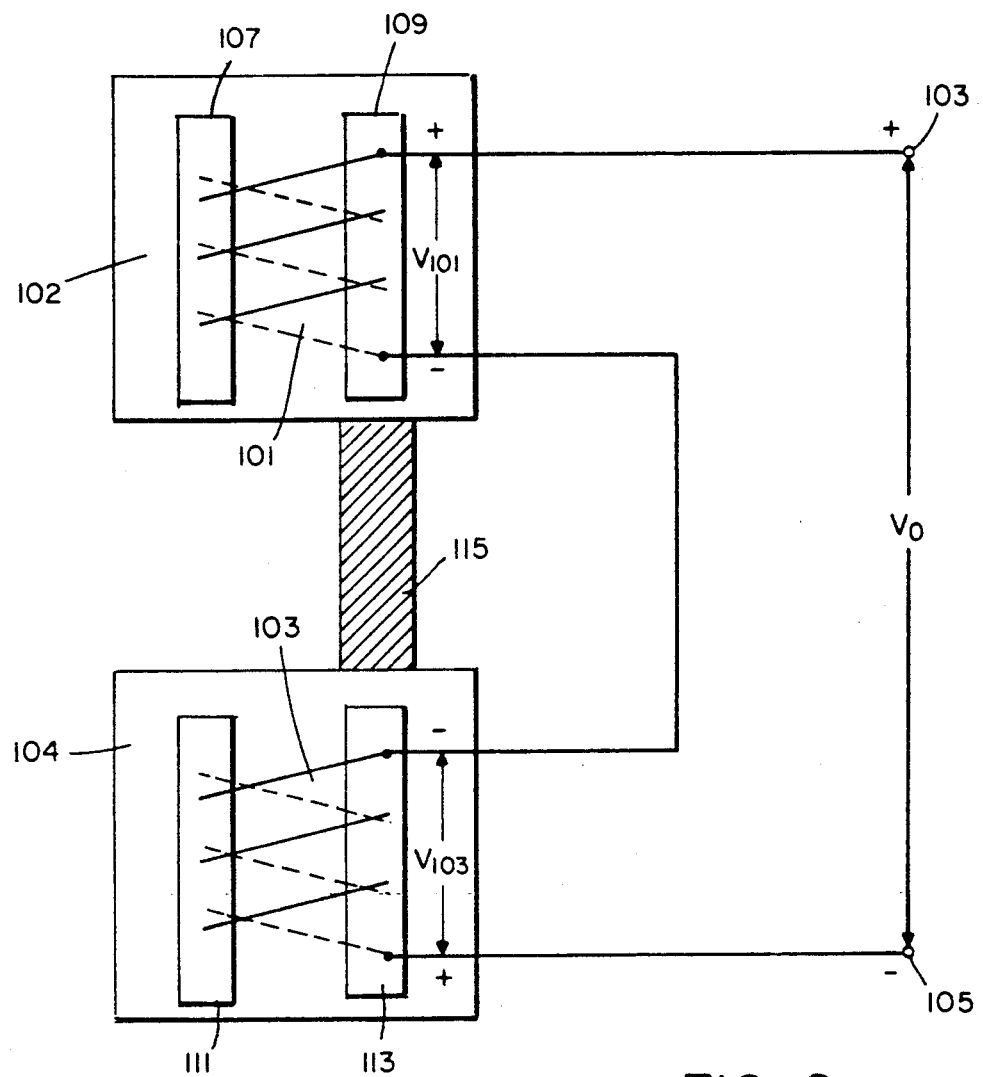
FIG. 2 is a schematic illustration of the thermal sensor of the present invention.

Referring FIG. 2 thermopile 101 and 103 of a differential temperature sensor 100 are shown schematically and are each used as part of individual detectors which the thermal radiation from two different locations. A voltage $V_{101}$ is developed between the positive and negative terminals of thermopile 101 and is proportional to the amount of thermal radiation sensed by thermopile 101. Similarly, voltage $V_{103}$ is developed between the positive and negative terminals of thermopile 103 which is proportional to the thermal radiation sensed by thermopile 103.

The negative voltage terminal of thermopile 101 is electrically connected to the negative voltage terminal of thermopile 103. This forces the voltage $V_D$ between terminal 103 and terminal 105 to be a differential voltage equal to $V_{101}-V_{103}$. Since the voltage of each thermopile is proportional to the thermal radiation that the thermopile senses, the voltage $V_D$ is proportional to the difference in thermal radiation sensed by the two thermopiles. The voltage $V_D$ is therefore a useful measure of the temperature difference between the location sensed by thermopile 101 and the location sensed by thermopile 103.

The voltage output by thermopile 101 is dependent on the temperature difference between a hot junction 107 and a cold junction 109 of the thermopile 101. Similarly, thermopile 103 develops its voltage output based on the thermal difference between hot junction 111 and cold junction 113. To provide an accurate indication of difference in target temperatures, it is necessary to keep the cold junctions of the thermopiles as close to one another in temperature as possible. Otherwise, each thermopile would be providing an output relative to a different cold junction reference temperature.

The thermopiles 101, 103 of the present embodiment are each contained in a separate package or "can" 102, 104 to which the cold junction is coupled. This allows each thermopile to be located wherever it is most convenient to the particular application. To keep the thermopile cold junctions at the same temperature, connector 115 is in thermal connection with both cold junction 109 and cold junction 113. The connector 115 is a material with low thermal impedance and in the preferred embodiment is a copper bar. A preferred method of connecting the cold junctions is by coupling the connector to the cans 102, 104 with thermal adhesive or solder. By thermally connecting the cold junctions 109, 113 of the thermopiles via connector 115, and by surrounding the connector and cans with an insulated housing, the thermopiles are held to the same reference cold junction temperature.

Figure 3:
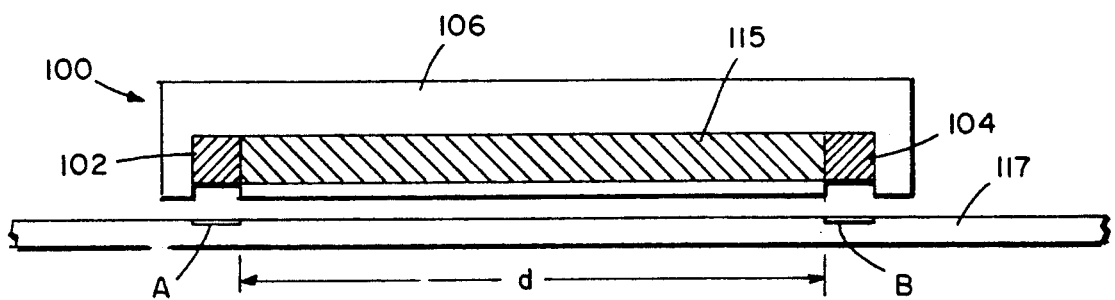
FIG 3 is a front view of a preferred embodiment of the thermal sensor of the present invention.

The relative positional and angular orientation of cans 102, 104 is set or adjusted to suit the requirements of the particular sensing application. As illustrated in FIG. 3, they may be displaced a significant distance d without the requirement of a lens.

As shown, the differential sensor 100 of FIG. 3 has two thermopile detectors packaged in separate cans 102, 104. The cold junctions of the thermopiles are thermally connected via the cans by copper bar connector 115. In addition, the housing 106 isolates the entire sensor 100 from the ambient atmosphere. The housing is either evacuated or is filled with a gas of high thermal impedance. Windows on the housing allow thermal radiation to pass through to the thermopiles of cans 102, 104, but keep the housing sealed tight.

The cans in FIG. 3 are separated by a distance d and are positioned to sense the temperature of two different sections of an object 117 so as to produce a differential temperature output. The distance d is great enough that the ambient temperature in the region of can 102 is substantially different than the ambient temperature in the region of can 104. The differential sensor 100 is nonetheless able to provide an accurate non-contact measurement of the temperature difference between the two regions of the object 117 due to the copper connector 115 between the thermopile cold junctions, so long as the assembly is thermally isolated from the environment.

A distinct advantage of the present invention is the ability of the differential sensor 100 to be very close to the location being measured. Since the shape and size of connector 115 is chosen for the particular sensing task, no focusing means are necessary with the differential sensor 100. Instead, the sensor 100 is placed with its cans 102, 104 very close to the locations being monitored. As a result, the cold junction temperature can be expected to be very close to the reference target temperature. From the following analysis this can be seen to provide improved accuracy when the thermopiles have slightly different gains.

As shown in FIG. 3, the differential sensor 100 is positioned to sense the temperature difference between the two regions of object 117, which are labeled A and B for convenience. The thermopile in can 102 detects radiation from region A while thermopile of can 104 senses radiation from region B. Using a wiring arrangement like that shown in FIG. 2, the output voltage $V_o$ of the sensor will be the difference between the output voltages of the two thermopiles, referred to as $V_A$ and $V_B$ for convenience. $V_A$ represents the output voltage of the thermopile sensing the temperature $T_A$ of region A. while $V_B$ represents the output voltage of the thermopile sensing the temperature $T_B$ of region B.

Each thermopile of the sensor has an inherent gain coefficient upon which the output voltage of that thermopile is dependent. Even when the thermopiles are matched, each might have a slightly different gain coefficient. The gain coefficient of the thermopile sensing region A is labeled $G_A$ while the gain coefficient of the thermopile sensing region B is labeled $G_B$. Therefore, the output voltages of the two thermopiles can be expressed as:

$$V_A=(T_A-T_o)G_A \text{ and } V_B=(T_B-T_o)G_B$$

where $T_o$ is the reference temperature of both thermally connected cold junctions.

In the present illustration, target B represents the reference (unchanging) temperature region of object 117. If the two gain constants are equal (i.e. $G_A=G_B=G$). then the thermopiles are perfectly matched and the sensor output may be expressed as:

$$V_o = V_A - V_B = G(T_A - T_o - T_B + T_o)$$
$$= G(T_A - T_B)$$

However, since a finite difference usually exists between the gain constants $G_A$ and $G_B$ (i e. $G_A \neq G_B$) then will be some slight difference and $V_o$ must be represented as:

$$V_o=(T_A-T_o)G_A-(T_B-T_o)G_B$$

But since region B is at the reference temperature of the target, $T_B$ is close to $T_o$ and $$(T_B-T_o)<<(T_A-T_o)$$

$V_o$ can therefore be approximated as:

$$V_o \delta (T_A-T_o)G_A \delta (T_A-T_B)G_A$$

Since this approximation depends on $T_B$ being close to $T_o$, the closer the sensor is to the object 117, the closer $T_o$ and $T_B$ are in temperature, and the better the approximation. Therefore the close proximity to the sensed object enhances the accuracy of the sensor.

Figure 4A:
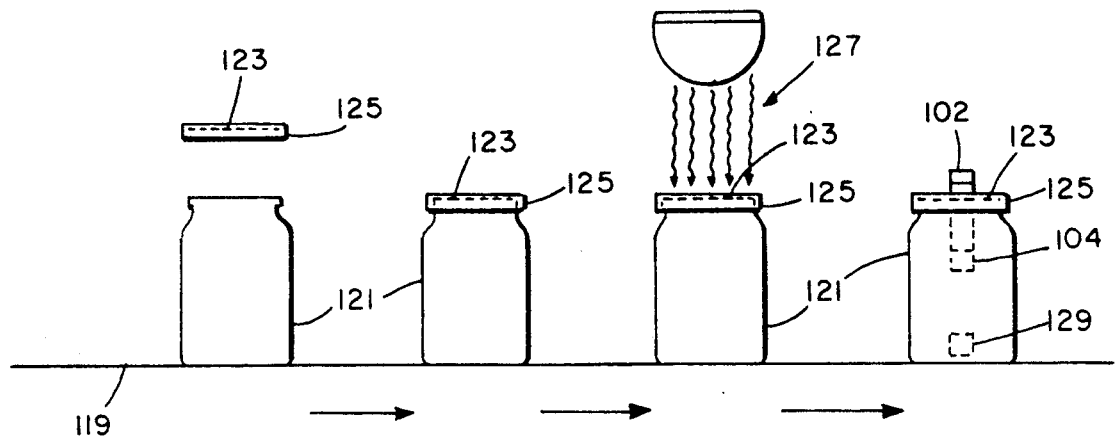
FIG. 4A is a front view of an assembly line process using the thermal sensor of the present invention.

Shown in FIG. 4A is an assembly line embodiment which uses the present invention. A conveyor belt 119 is moving in the direction of the arrows and carries bottles 121 from one station to the next. In this embodiment, the bottles are plastic pill bottles for off-the-shelf medicine. As part of the capping procedure, the bottles 121 are each provided with a tamper-proof aluminum seal 123. The seal 123 is delivered to the bottle 121 with the bottle cap 125 and has a ring of heat-activated adhesive along its edge on the side of the seal facing the bottle 121. After the cap 125 is placed on the bottle, induction heating 127 is applied to the top of the bottle to activate the adhesive on the seal 123, thereby bonding the seal to the bottle 121.

In the above packaging procedure, the seal 123 is kept inside the bottle cap 125 during its delivery to the bottle 121. A visual inspection therefore can not be made to verify that the bottle has been sealed. However, during the heating process 127, eddy currents are generated in the foil seal 123 and detectable heat is retained in the seal for a short period of time. After heating, the bottle 121 is therefore moved to a heat detection station to verify the presence of the seal 123. At this station, the differential sensor 100 of the present invention is used to detect a difference in temperature between the top of the bottle 121 and a reference point along the side of the bottle. Although the necessary configuration of the sensing task would present a problem for a conventional differential radiation detector, sensor 100 is easily adapted to the situation.

Figure 4B:
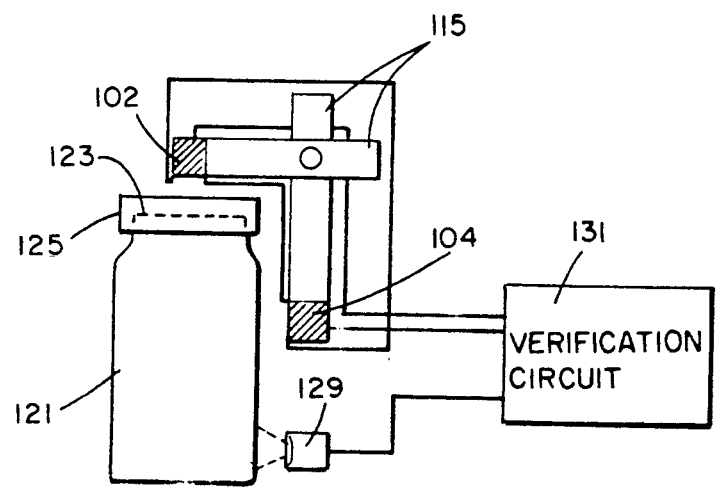
FIG. 4B is a side view of the temperature sensing station of the process of FIG. 4A.

FIG. 4B is a side view of the heat detection station. The bottle 121 moves to the heat detection station such that its top is close to can 102 and its side is the reference point close to can 104. In this embodiment, connector 115 is a two-piece adjustable copper bar which allows the cans 102, 104 to be at two different positions and two different angular orientations. The two pieces of the connector are slidable and pivotable relative to one another. The connector 115 connects the cold junctions of the two thermopiles by contacting the surface of both cans 102, 104, and therefore keeps the thermopiles at the same reference temperature. If the foil seal 123 is present and has been properly heated by the induction heating 127, a sufficient differential temperature is measured by the sensor 100 and the sealing procedure is considered successful. However, if no foil is present, or if the foil has not been properly heated, the thermal difference measured by the sensor 100 is insufficient and the sealing process is deemed a failure.

To properly automate the above inspection procedure, a photoelectric switch 129 is provided to detect when a bottle 121 is present at the heat detection station. This allows a verification circuit 131 to be provided which synchronizes the photodetector signal with the signal of sensor 100. The photoelectric switch 129 and the verification circuit 131 are shown as being separate from sensor 100, but either or both may be alternatively be housed with the sensor 100 in housing 106.

Figure 5:
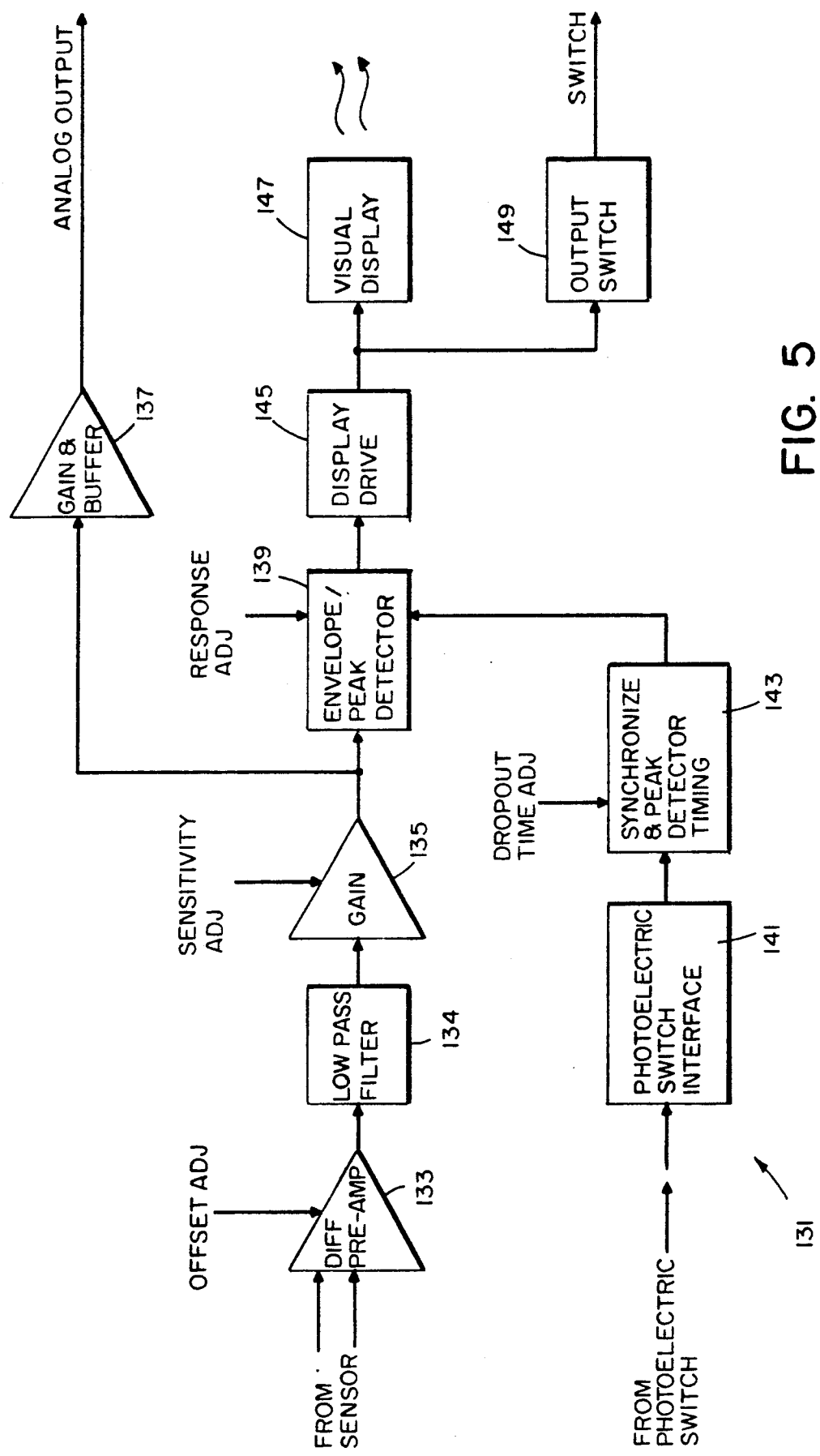
FIG. 5 is a schematic of the verification circuit used with the process of FIG. 4.

The verification circuit 131 is shown schematically in FIG. 5. The thermopile signals are input from the sensor 100 to a differential pre-amplifier 133 which has a manual offset adjustment. The output of pre-amplifier 133 is representative of the output difference between the two thermopiles, and is input through low pass filter 134 to a gain amplifier 135. The gain amplifier 135 has a manual sensitivity adjustment to control the magnitude of the output signal. The output of the amplifier 135 is input to both gain and buffer amplifier 137 and to envelope/peak detector 139. Amplifier 137 generates an analog output of the differential signal. Envelope/peak detector 139 coordinates the output of amplifier 135 with a signal from the photoelectric switch 129.

The photoelectric switch 131 inputs a signal through switch interface 141. This signal is modified by synchronizer 143 which has a manual input with which the timing of the photoelectric switch signal is manually adjusted. The synchronized switch signal is input to the envelope/peak detector 139. If the detector 139 receives a signal from gain amplifier 135 when the synchronizer 143 signal shows that a bottle is present, the output to display drive 145 indicates that the detection is successful. The display drive then drives LED display 147 to indicate that the presence of the seal is verified. Since the display is driven through an envelope detector circuit, its output is prevented from falling quickly when a bottle 121 is not present. Only a missed thermal detection when a bottle should be present causes a drop in the output substantial enough to cause an alarm. The display drive 145 also feeds output switch 149 which sounds an alarm signal when the heated seal is not detected. If desired, the output switch can also be implemented to stop the conveyor belt when such a failure is detected.

Figure 6A:
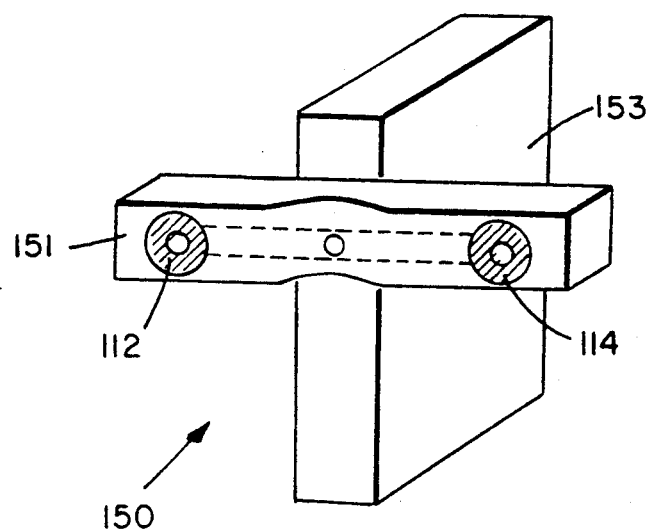
FIG. 6A is a perspective view of a chiropractic measurement device using the present invention.
Figure 6B:
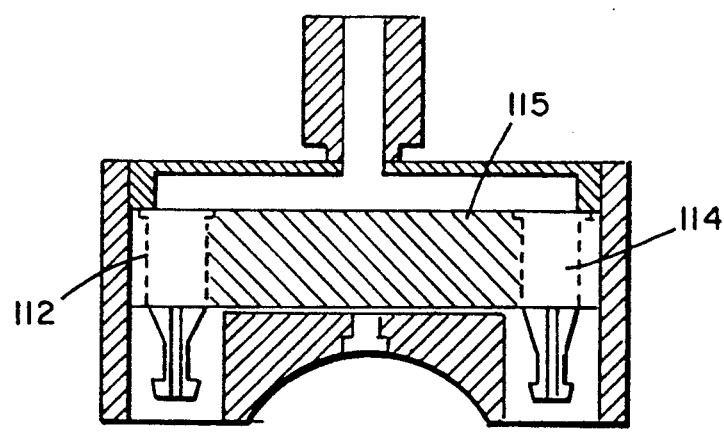
FIG. 6B is a cross sectional top view of the chiropractic measuring device of FIG. 6A.

Another preferred embodiment of the differential radiation sensor 100 is shown in FIG. 6A and FIG. 6B. FIG. 6A shows a perspective view of a chiropractic measuring device 150 having sensor housing 151 within which is housed differential sensor 100. The housing 151 is mounted on sensor body 153. Within housing 151 are cans 112, 114 enclosing thermopiles 101, 103. The cans 112, 114 are shown more clearly in the cross sectional top view of FIG. 6B.

The cans 112, 114 are different from cans 102, 104 in shape and limit the viewing direction of the thermopiles 101, 103. The cold junctions of thermopiles 101, 103 are thermally connected within the housing 151 by copper bar connector 115 which contacts both cans 112, 114. This keeps the reference points of the thermopiles equal and preserves the accuracy of the differential measurement.

The chiropractic device 150 of FIGS. 6A and 6B is a measuring tool for detecting nerve damage on either side of a subjects spine. It is well known in the chiropractic field that such neural damage near the spine results in vasal constriction of nearby blood vessels. This vasal constriction reduces blood flow in the region of nerve damage. Previously, the constriction has been detected with a pair of thermocouples dragged along to either side of the spine. To detect such an injury with the present invention, the measuring device 150 is placed with one can positioned in front of either side of the subject's spine. Each thermopile 101, 103 detects the thermal radiation emitted from one side of the spine. The differential sensor compares the measurements of the thermopiles 101, 103, and if there is no difference, the measurement output is negative. However, if one of the thermopiles outputs a significantly smaller signal than the other, an output signal is generated which indicates that some nueral damage may exist in that region.

The chiropractic device 150 uses the differential radiation detector 100 to compare one side of the spine to the other. Since ordinarily both sides of a subject's spine should have an equal thermal output, the differential measurement allows an accurate determination of neural damage without the inaccuracies of an absolute temperature measurement. An output display such as a plotter, a meter, or an LED display such as that used with the assembly line embodiment, displays the temperature difference between the two sides of the spine. An output such as a light or an audible beep can also be used to indicate when there is a significant difference between the thermal radiation sensed by the two thermopiles 101, 103. Holding the device 150 in hand, a doctor draws the device slowly down a patient's back keeping the radiation guides to either side of the spine. When a significant difference is detected in the thermal radiation to either side of the spine, the output of the device 150 is noted by the doctor and further examination can be concentrated on the region indicated.

Figure 7:
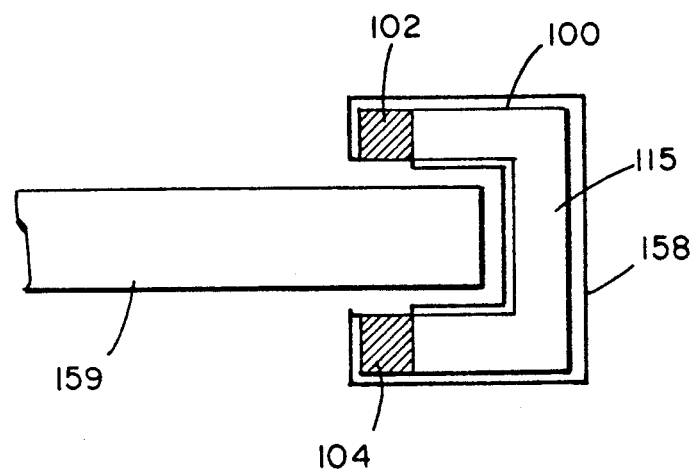
FIG. 7 is a cross sectional view of an embodiment using the present invention to measure the differential temperature between two sides of an object.

Another embodiment of the present invention, is demonstrated in FIG. 7. As shown, the connector 115 is of a U-shape connecting cans 102, 104 in housing 158. This allows the thermopiles to be positioned on either side of object 159. The differential sensor thus gives a measurement of the temperature difference between the two sides of the object 159 The size of connector 115 may be adjusted to sense further toward the center of the object 159 if necessary.

Figure 8:
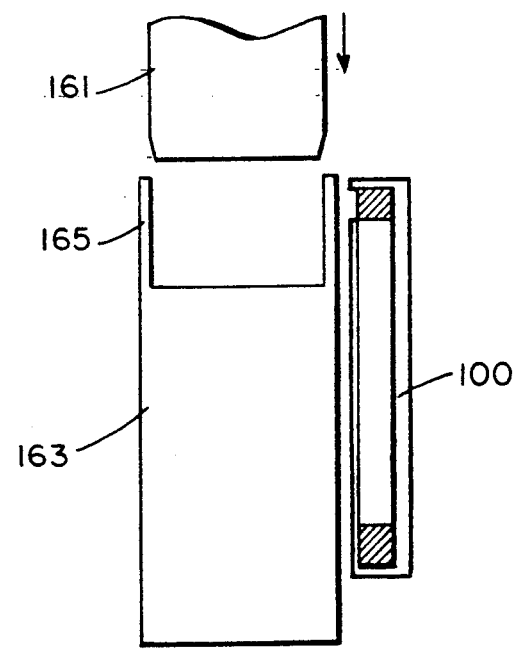
FIG. 8 is a cross sectional view of an embodiment of the present invention using the thermal sensor to detect the assembly of press to fit parts.

Still another embodiment of the differential sensor 100 is shown in FIG. 8. In automated press-to-fit manufacturing applications, a proper assembly may not always be made However, a simple detection scheme is available with the differential thermal detector of the present invention. In the assembly process of FIG. 8, a first part 161 is automatically inserted into a second part 163. Differential sensor 100 is adjacent part 163 during assembly such that the thermopile in can 102 is sensing the thermal radiation from top portion 165, while the thermopile in can 104 is sensing a reference surface further down the body of the part 163. As the parts are forced together, a small amount of heat is generated. That heat results in thermal radiation detected by thermopile 101. The differential sensor 100 detects the thermal difference between the two different locations and outputs a signal indicating that the assembly is successful.

One aspect of the differential sensor of the present invention is its ability to make an accurate measurement quickly. An embodiment which amply demonstrates this is the factory installation of an automobile windshield. Prior to assembly, the windshield is given a coating of a primer along its outer edge. The primer is a volatile liquid which prepares the edge of the windshield to receive a sealant. The layer of primer is wiped with a squeegee after application. After wiping, the primer quickly evaporates. Due to this evaporation, the surface of the windshield under the primer is cooled slightly. To verify the presence of the primer, the windshield is passed by the differential thermal sensor of the present invention. If the primer is present in the required location, the differential sensor detects the temperature difference and quickly responds to confirm its presence.

Since, in general, the presence of a liquid will provide an evaporative cooling effect to a surface on which it is present, the differential sensor of the present invention is appropriate for accurately detecting the pressure of such liquids. The high resolution and quick response of the differential sensor allow detection of extremely thin layers of liquid. By comparing a region of an object having a coating of a liquid to a dry region of the same object, the presence of the liquid is quickly and accurately confirmed.

While the invention has been particularly shown and described with reference to a preferred embodiment thereof, it will be understood by those skilled in the art that various changes in form and details may be made therein without departing from the spirit and scope of the invention as defined by the appended claims.

I claim:

1. A radiation detector comprising:
    a first thermopile in a first can sensing thermal radiation from a target area and generating a signal indicative thereof;
    a second thermopile in a second can sensing thermal radiation from a reference area and generating a signal indicative thereof;
    a connector of low thermal impedance thermally connecting a cold junction of the first thermopile to a cold junction of the second thermopile; and
    an output signal developed from the signal generated by the first thermopile and the signal generated by the second thermopile, the output signal being indicative of thermal difference between the target area and the reference area.

2. A radiation detector according to claim 1 wherein the connector is angled.

3. A radiation detector according to claim 1 wherein the connector is adjustable in length.

4. A radiation detector according to claim 1 wherein the connector comprises a plurality of pivotable sections.

5. A radiation detector according to claim 1 wherein the thermal impedance between said cold junctions and the ambient atmosphere about the cold junctions is at least about 1000 times greater than the thermal impedance of the connector.

6. A radiation detector according to claim 1 further comprising a visual display.

7. A radiation detector according to claim 6 wherein the display is an LED display.

8. A radiation detector according to claim 1 further comprising an alarm which is triggered by the output signal exceeding a predetermined limit.

9. A radiation detector according to claim 1 wherein each thermopile has a different angular orientation.

10. A radiation detector according to claim 1 wherein the first thermopile is proximate to the target area.

11. A radiation detector according to claim 1 wherein the second thermopile is proximate to the reference area.

12. A radiation detector according to claim 11 wherein the cold junction of the second thermopile is at approximately the same temperature as the reference area.

13. A radiation detector according to claim 1 further comprising a housing enclosing both the first and second cans, the housing thermally insulating the cans from an external atmosphere.

14. A radiation detector according to claim 1 wherein the cold junctions of the first and second thermopiles are thermally connected to the first and second cans, respectively.

15. A radiation detector according to claim 14 wherein the connector thermally connects the first can to the second can.

16. A radiation detector comprising:
    a first thermopile having a first angular orientation, the first thermopile sensing thermal radiation from a target area and generating a signal indicative thereof;

a second thermopile having a second angular orientation distinctly different from said first angular orientation, the second thermopile sensing thermal radiation from a reference area and generating a signal indicative thereof.;

a connector of low thermal impedance thermally connecting a cold junction of the first thermopile to a cold junction of the second thermopile; and an output signal developed from the signal generated by the first thermopile and the signal generated by the second thermopile, the output signal being indicative of thermal difference between the target area and the reference area.

17. A radiation detector according to claim 16 wherein the connector is angled.

18. A radiation detector according to claim 16 wherein the connector is adjustable in length.

19. A radiation detector according to claim 16 wherein the connector comprises a plurality of pivotable sections.

20. A radiation detector according to claim 16 wherein the thermal impedance between said cold junctions and the ambient atmosphere about the cold junctions is at least about 1000 times greater than the thermal impedance of the connector.

21. A radiation detector according to claim 16 further comprising a visual display.

22. A radiation detector according to claim 21 wherein the display is an LED display.

23. A radiation detector according to claim 16 further comprising an alarm triggered by an output signal exceeding a predetermined limit.

24. A radiation detector according to claim 16 wherein the second thermopile is proximate to the reference area.

25. A radiation detector according to claim 24 wherein the cold junction of the second thermopile is at approximately the same temperature as the reference area.

26. A radiation detector according to claim 16 further comprising first and second isolated cans in which the first and second thermopiles are respectively enclosed.

27. A radiation detector according to claim 26 wherein the cold junctions of the first and second thermopiles are thermally connected to the first an second cans, respectively, and the connector thermally connects the first and second cans.

28. A radiation detector comprising
a first thermopile sensing thermal radiation from a target area and generating a signal indicative thereof, the first thermopile being proximate to the target area;

a second thermopile sensing thermal radiation from a reference area and generating a signal indicative thereof, the second thermopile being proximate to the reference area;

a connector of low thermal impedance thermally connecting a cold junction of the first thermopile to a cold junction of the second thermopile; and an output signal developed from the signal generated by the first thermopile and the signal generated by the second thermopile, the output signal being indicative of thermal difference between the target area and the reference area.

29. A radiation detector according to claim 28 wherein the connector is angled.

30. A radiation detector according to claim 28 wherein the connector is adjustable in length.

31. A radiation detector according to claim 28 wherein the connector comprises a plurality of pivotable sections.

32. A radiation detector according to claim 28 wherein the thermal impedance between said cold junctions and the ambient atmosphere about the cold junctions is at least about 1000 times greater than the thermal impedance of the connector.

33. A radiation detector according to claim 28 further comprising a visual display.

34. A radiation detector according to claim 33 wherein the display is an LED display.

35. A radiation detector according to claim 28 further comprising an alarm which is triggered by the output signal exceeding a predetermined limit.

36. A radiation detector according to claim 28 wherein each thermopile has a different angular orientation.

37. A radiation detector according to claim 28 wherein cold junction of the second thermopile is at approximately the same temperature as the reference area.

38. A radiation detector according to claim 28 further comprising first and second isolated cans in which the first and second thermopiles are respectively enclosed.

39. A radiation detector according to claim 38 wherein the cold junctions of the first and second thermopiles are thermally connected to the first and second cans, respectively, and the connector provides a thermal connection between the first and second cans.

40. A method of performing a differential temperature measurement comprising:
providing a first thermopile in a first housing which senses thermal radiation from a target area and generates a signal indicative thereof;

providing a second thermopile in a second housing which senses thermal radiation from a reference area and generates a signal indicative thereof;

thermally connecting a cold junction of the first thermopile to a cold junction of the second thermopile with a connector of low thermal impedance;

developing an output signal from the signal generated by the first thermopile and the signal generated by the second thermopile, the output signal being indicative of thermal difference between the target area and the reference area.

41. A method according to claim 40 wherein the thermopiles have substantially different viewing directions.

42. A method according to claim 40 further comprising displaying a representation of the output signal on a visual display.

43. A method according to claim 40 further comprising triggering an alarm when the magnitude of the output signal exceeds a predetermined limit.

44. A method according to claim 40 further comprising positioning the second thermopile proximate to the reference area.

45. A method of measuring the temperature difference between two different areas of a subject, the method comprising:
providing a first thermopile in a first housing;
positioning the first thermopile such that it detects thermal radiation from a target area on the subject and generates an output signal indicative thereof;
providing a second thermopile in a second housing;

positioning the second thermopile such that it detects thermal radiation from a reference area on the subject and generates an output signal indicative thereof;

thermally connecting a cold junction of the first thermopile with a cold junction of the second thermopile with a connector of low thermal impedance; and developing an output signal from the signal generated by the first thermopile and the signal generated by the second thermopile, the signal being indicative of thermal difference between the target area and the reference area.

46. A method according to claim 45 wherein the temperature measurement is performed as an inspection step in an assembly line process.

47. A method according to claim 45 further comprising coordinating the temperature measurement with a photoelectric switch which detects when the subject is present.

48. A method according to claim 45 wherein the target area and the reference area are on different sides of said object.

49. A method according to claim 45 wherein measured temperature variations are caused by mechanical stress in the target area of the subject.

50. A method of performing an examination on a subject, the method comprising:

providing a first thermopile in a first housing which senses thermal radiation from a first area and generates a signal indicative thereof;

providing a second thermopile in a second housing which senses thermal radiation from a second area and generates a signal indicative thereof;

thermally connecting a cold junction of the first thermopile to a cold junction of the second thermopile with a connector of low thermal impedance;

positioning the thermopiles such that they each detect thermal radiation from one side of the subject's spine;

simultaneously drawing the thermopiles along the subject's spine; and developing an output signal from the signal generated by the first thermopile and the signal generated by the second thermopile, the output signal being indicative of thermal difference between the first area and the second area.

51. A method according to claim 50 further comprising bracing the thermopiles relative to one another with a common casing.

52. A method according to claim 51 further comprising providing a shaft attached to the casing.

53. A method according to claim 50 further comprising providing a first radiation guide and a second radiation guide limiting the viewing direction of the first thermopile and the second thermopile, respectively.

54. A method according to claim 50 further comprising providing a visual display for displaying the output signal.

55. A method according to claim 54 wherein the visual display is an LED display.

56. A method according to claim 50 further comprising providing in audible or visual output indicating when the output signal exceeds a predetermined level.

* * * * *